United States Patent
Parrott

(10) Patent No.: US 10,858,493 B2
(45) Date of Patent: *Dec. 8, 2020

(54) CHEMICAL RECYCLING OF POLYETHYLENE TEREPHTHALATE BY MICROWAVE IRRADIATION

(71) Applicant: The University of North Carolina at Chapel Hill, Chapel Hill, NC (US)

(72) Inventor: Matthew Parrott, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/662,168

(22) Filed: Oct. 24, 2019

(65) Prior Publication Data

US 2020/0056009 A1 Feb. 20, 2020

Related U.S. Application Data

(63) Continuation of application No. 15/773,503, filed as application No. PCT/US2016/062682 on Nov. 18, 2016, now Pat. No. 10,508,186.

(60) Provisional application No. 62/258,116, filed on Nov. 20, 2015.

(51) Int. Cl.
| | | |
|---|---|---|
| *C07C 67/48* | (2006.01) | |
| *C08J 11/16* | (2006.01) | |
| *C08J 11/24* | (2006.01) | |
| *C07C 67/54* | (2006.01) | |
| *C08J 11/26* | (2006.01) | |
| *C08J 11/28* | (2006.01) | |

(52) U.S. Cl.
CPC ............... *C08J 11/16* (2013.01); *C07C 67/48* (2013.01); *C07C 67/54* (2013.01); *C08J 11/24* (2013.01); *C08J 11/26* (2013.01); *C08J 11/28* (2013.01); *C08J 2367/02* (2013.01); *C08J 2367/04* (2013.01); *Y02W 30/62* (2015.05)

(58) Field of Classification Search
CPC . C07C 67/48; C07C 67/54; C08J 11/16; C08J 11/24; C08J 11/26; C08J 11/28; C08J 2367/02; C08J 2367/04; Y02W 30/705; Y02W 30/706

See application file for complete search history.

(56) References Cited

U.S. PATENT DOCUMENTS

| | | |
|---|---|---|
| 5,481,024 A | 1/1996 | Hertenstein et al. |
| 6,916,936 B2 | 7/2005 | Hedrick et al. |
| 2005/0096482 A1 | 5/2005 | Tamada et al. |

FOREIGN PATENT DOCUMENTS

| | | | |
|---|---|---|---|
| CA | 2337597 | | 8/2001 |
| CN | 101177503 | | 5/2008 |
| CN | 104479168 | | 4/2015 |
| DE | 69803212 | | 7/2002 |
| EP | 0583743 | | 8/1993 |
| EP | 1134211 | | 9/2001 |
| EP | 1023369 | | 1/2002 |
| JP | 2002060474 | | 2/2002 |
| JP | 04486237 | | 3/2002 |
| JP | 2006335856 | | 12/2006 |
| JP | 2012067200 | | 4/2012 |
| JP | 2013057006 | | 3/2013 |
| KR | 415465 | | 5/2005 |
| WO | 97/46611 | | 12/1997 |
| WO | 2009010435 | | 1/2009 |
| WO | WO2009010435 | * | 1/2009 |
| WO | 2012/121985 | | 9/2012 |
| WO | 2013/014650 | | 1/2013 |
| WO | 2014/093991 | | 6/2014 |
| WO | 2014/093995 | | 6/2014 |
| WO | 2017087752 | | 5/2017 |

OTHER PUBLICATIONS

Achilias et al. "Glycolytic depolymerization of PET waste in a microwave reactor" Journal of Applied Polymer Science, 118(5):3066-3073 (2010).
Al-Sabagh et al. "Greener routes for recycling of polyethylene terephthalate" Egyptian Journal of Petroleum, 25:53-64 (2016).
Alnaqbi et al. "Microwave assisted glycolysis of poly(ethylene terephthalate) catalyzed by 1-butyl-3-methylimidazolium bromide ionic liquid" Journal of Applied Polymer Science, 132(12):41666 (2015).
Bartolome et al. "Recent Developments in the Chemical Recycling of PET" Material Recycling—Trends and Perspectives, Chapter 2, Intech, pp. 65-84 (2012).
Curnutte, B. "Principles of Microwave Radiation" Journal of Food Protection, 43(8):618-624 (1980).
Database WPI/Thomson, Week 200711, XP-002765464; JP 2006 335856 (ZH Kumamoto Techno. Sangyo Zaidan) (2 pages) (Dec. 14, 2006) (Abstract).
Database WPI/Thomson, Week 200857, XP-002765465; CN 101 177 503 (Univ. Zhejiang) (2 pages) (May 14, 2008) (Abstract).
Database WPI/Thomson, Week 201543, XP-002765463; CN 104 479 168 (Guangdong Shuye Environmental Technology) (3 pages) (Apr. 1, 2015) (Abstract).

(Continued)

Primary Examiner — Yevgeny Valenrod
Assistant Examiner — Blaine G Doletski
(74) Attorney, Agent, or Firm — Myers Bigel, P.A.

(57) ABSTRACT

A process for chemically recycling polyethylene terephthalate (PET) which utilizes a microwave absorber to optimize glycolytic depolymerization of PET via microwave irradiation. The method of chemically degrading PET to its reactive intermediate, bis(2-hydroxyethyl) terephthalate (BHET), is carried out by: (a) combining PET with ethylene glycol and a catalytic system comprising a catalyst and a microwave absorber to produce a heterogeneous reaction mixture; and then (b) heating by microwave irradiating the reaction mixture to a temperature sufficient to produce a reaction product comprising BHET. The BHET monomer then can be purified and re-polymerized to form new, virgin PET.

16 Claims, No Drawings

(56) References Cited

OTHER PUBLICATIONS

Fukushima et al. "Organocatalytic depolymerization of poly(ethylene terephthalate)" Journal of Polymer Science: Part A, 49(5):1273-1281 (2011).

Fukushima et al. "Unexpected efficiency of cyclic amidine catalysts in depolymerizing poly(ethylene terephthalate)" Journal of Polymer Science: Part A, 51(7):1606-1611 (2013).

George et al. "Recent Developments in the Chemical Recycling of Postconsumer Poly(ethylene terephthalate) Waste" Industrial & Engineering Chemistry Research, 53:14185-14198 (2014).

Imran et al. "Sub- and supercritical glycolysis of polyethylene terephthalate (PET) into the monomer bis(2-hydroxyethyl) terephthalate (BHET)" Polymer Degradation and Stability, 95(9):1686-1693 (2010).

International Preliminary Report on Patentability corresponding to International Patent Application No. PCT/US2016/062682 (7 pages) (dated May 31, 2018).

International Search Report and the Written Opinion of the International Searching Authority corresponding to International Patent Application No. PCT/US2016/062682 (12 pages) (dated Jan. 9, 2017).

Lopez-Fonseca et al. "Chemical recycling of post-consumer PET wastes by glycolysis in the presence of metal salts" Polymer Degradation and Stability, 95(6):1022-1028 (2010).

Pingale et al. "Glycolysis of postconsumer polyethylene terephthalate waste" Journal of Applied Polymer Science, 115(1):249-254 (2010).

Pingale et al. "Microwave assisted ecofriendly recycling of poly (ethylene terephthalate) bottle waste" European Polymer Journal, 44(12):4151-4156 (2008).

Pticek Sirocic et al. "Chemical Recycling of Postconsumer Poly-(ethylene-terephthalate) Bottles—Depolymerization Study" Chemical and Biochemical Engineering Quarterly, 27(1):65-71 (2013).

Siddiqui et al. "Recycling of poly(ethylene terephthalate) waste through methanolic pyrolysis in a microwave reactor" Journal of Analytical and Applied Pyrolysis, 98:214-220 (2012).

Troev et al. "A novel catalyst for the glycolysis of poly(ethylene terephthalate)" Journal of Applied Polymer Science, 90(4):1148-1152 (2003).

Tsubaki et al. "Microwave-assisted Hydrothermal Hydrolysis of Maltose with Addition of Microwave Absorbing Agents" Procedia Chemistry, 4:288-293 (2012).

Welle, Frank "Twenty years of PET bottle to bottle recycling—An overview" Resources, Conservation and Recycling, 55:865-875 (2011).

Xi et al. "Study on depolymerization of waste polyethylene terephthalate into monomer of bis(2-hydroxyethyl terephthalate)" Polymer Degradation and Stability, 87(1):117-120 (2005).

International Search Report and the Written Opinion of the International Searching Authority corresponding to International Patent Application No. PCT/US2019/052263 (24 pages) (dated Oct. 31, 2019).

\* cited by examiner

CHEMICAL RECYCLING OF POLYETHYLENE TEREPHTHALATE BY MICROWAVE IRRADIATION

CROSS-REFERENCE TO RELATED APPLICATIONS

This application is a continuation application of U.S. patent application Ser. No. 15/773,503, filed May 3, 2018, which is a 35 U.S.C. § 371 national stage application of PCT International Application No. PCT/US2016/062682, filed Nov. 18, 2016, which claims the benefit of U.S. Provisional Application No. U.S. 62/258,116, filed Nov. 20, 2015, the contents of which are incorporated herein in their entireties by reference.

STATEMENT REGARDING FEDERALLY SPONSORED RESEARCH OR DEVELOPMENT

This invention was made with government support under Grant No. TR001111 awarded by the National Institutes of Health. The government has certain rights in the invention.

BACKGROUND OF THE INVENTION

Polyethylene terephthalate (PET, PETE, or recycle symbol "1") is one of the most frequently used consumer plastics. Everyday products made from PET include: water bottles, soda bottles, food packaging, clothing, carpeting and filler for furniture. The United States alone consumes more than two million tons of PET plastic annually, with demand increasing each year. This demand puts a growing strain on local landfills and an ever-increasing burden on the environment, as PET is produced from petrochemicals.

To address increasing PET demand while reducing the environmental impact of PET production, efforts to recycle PET have been employed. Although the most common PET recycling techniques are in-plant and mechanical methods, chemical recycling is considered to be the only sustainable option for the recycling of PET.

Chemical recycling is the act of breaking the polymer down to either its original starting materials or its reactive intermediates. Breaking the PET down to small molecules allows recyclers the ability to remove contaminants (dyes, adhesives, bottle caps) using practices from industrial chemistry (precipitation, decantation, solvation etc.). By breaking down the PET into monomers and oligomers that are readily purified, the finished polymer is suitable for food-contact without any further treatment.

Glycolysis of PET is one of the most widely studied chemical recycling processes. PET depolymerization by glycolysis involves heating PET and ethylene glycol in the presence of a catalyst. This results in the degradation of PET to a reactive monomer-bis(2-hydroxyethyl) terephthalate monomer (BHET)—which then can be purified and re-polymerized to form new, virgin PET.

Because chemical PET recycling via glycolysis requires exotic catalysts and significant amounts of energy (heat), current research has been focused on discovering new catalysts, optimizing reaction conditions, and implementing new processes for achieving more efficient degradation of PET. One area of particular interest is the utilization of microwave irradiation to degrade PET. Microwave heating leads to extremely short reaction times with much higher energy-to-heat conversion when compared to conventional heating means. However, even with the use of microwave irradiation, PET recycling via glycolysis is still cost prohibitive due to the energy requirements.

SUMMARY OF THE INVENTION

The invention disclosed herein is directed to a method of chemically recycling polyethylene terephthalate (PET) using microwave irradiation and a mixed catalytic system comprising a catalyst and a microwave absorber. By utilizing a mixed catalytic system that features a microwave absorber, glycolytic depolymerization of PET via microwave irradiation can be optimized to provide a process that is significantly more energy efficient than current chemical recycling techniques.

In a particular embodiment exemplifying the principles of the invention, a method of chemically degrading PET to its reactive intermediate, bis(2-hydroxyethyl) terephthalate (BHET), is carried out by: (a) combining PET with ethylene glycol and a catalytic system comprising a catalyst and a microwave absorber to produce a heterogeneous reaction mixture; and then (b) heating the reaction mixture by microwave irradiation to a temperature sufficient to produce a reaction product comprising BHET. The resultant BHET monomers and BHET oligomers can then can be purified and re-polymerized to form new, virgin PET.

The above summary is not intended to describe each illustrated embodiment or every possible implementation. These and other features, aspects, and advantages of the present invention will become better understood with regard to the following description, appended claims, and accompanying drawings.

DETAILED DESCRIPTION

An improved method of glycolytic depolymerization of polyethylene terephthalate (PET) via microwave irradiation is disclosed herein. PET is a semi-crystalline resin formed by the condensation polymerization of terephthalic acid (TA) and ethylene glycol (EG). The polymerization requires two steps: 1) formation of reactive intermediates, typically BHET monomers and/or PET oligomers, and 2) melt polymerization of the reactive intermediates:

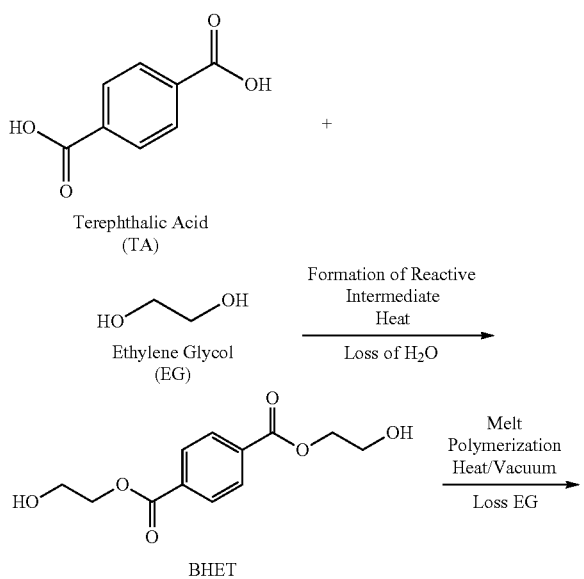

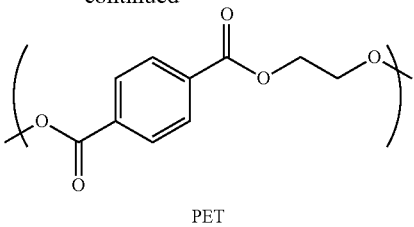

PET

Water is removed during the first step, with excess ethylene glycol being removed during the second step. The presence of water and ethylene glycol significantly hinders the clarity, strength, molecular weight, and intrinsic viscosity. Intrinsic viscosity is the most vital characteristic, and PET intrinsic viscosities can range from 0.4 deciliters per gram (dl/g) to 1.0 dl/g. Different intrinsic viscosities lead to different PET grades for numerous products including: fiber, textiles, film and food products. Food grade PET (water bottles, soda bottles and packaging) has an intrinsic viscosity between 0.70-0.85 dl/g. This equates to a polymer with an average molecular weight between 18,000-30,000 g/mol containing between 100-150 repeat units.

Chemical recycling via glycolysis involves heating PET and ethylene glycol in the presence of a catalyst. This results in the degradation of PET down to bis(2-hydroxyethyl) terephthalate ($C_6H_4(CO_2CH_2CH_2OH)_2$) monomer (BHET) and/or oligomers of PET:

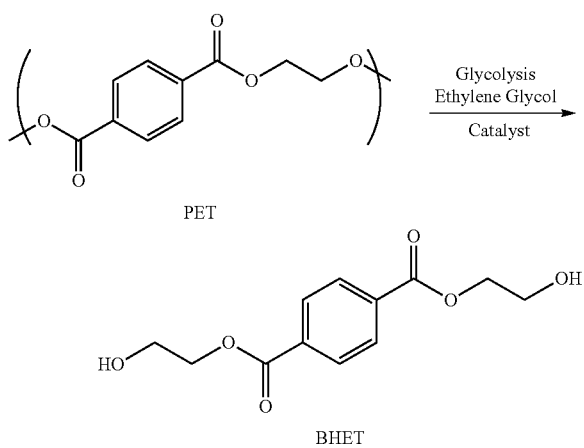

Because the BHET monomer is the reactive intermediate created during the initial step of the synthesis of virgin PET, the initial step in the synthesis of PET can be avoiding when forming new PET from glycolytic depolymerized PET. Moreover, BHET can be added directly to existing manufacturing infrastructure when synthesizing new PET, thereby allowing for the use of both new petrochemical feedstock and recycled PET feedstock.

In an embodiment exemplifying the principles of the invention, the chemical recycling of PET is carried out by glycolytic depolymerization of PET via microwave irradiation. The process of forming BHET from PET comprises the combining of PET, ethylene glycol, and a catalytic system to form a reaction mixture, with the catalytic system comprising both a catalyst and a microwave absorber. The reaction mixture is then heated by microwave irradiation in order to degrade the PET to its reactive intermediate(s), forming a reaction product comprising BHET monomers. In certain embodiments, the reaction mixture can be heated by microwaves irradiating the reaction mixture to a temperature greater than the boiling point of ethylene glycol. In other embodiments, the reaction mixture can be heated to a temperature of at least the melting point of the PET. Heating may be carried out at atmospheric pressure, or optionally at an elevated pressure, for example, 0 or 1 to 30 bar, or more. The reaction may be carried out open to the atmosphere, or may be in a closed vessel, optionally under an inert blanket or atmosphere (e.g., nitrogen, argon, etc.)

According to a further embodiment exemplifying the principles of the invention, and once the PET has been degraded to its reactive intermediate(s), the BHET can be precipitated and separated from the reaction product to produce solid BHET and a depleted reaction product. The depleted reaction product will comprise ethylene glycol and residual BHET that did not precipitate, along with any residual catalyst and/or microwave absorber. In an embodiment, the process of precipitating the BHET from the reaction product can be carried out by cooling the ethylene glycol to a temperature less than 60° C. In some embodiments, water may optionally be mixed into the reaction to facilitate the precipitation. In an embodiment, the process of separating the BHET from the reaction product can be carried out by sedimentation, centrifugation, filtration, or a combination thereof. In further embodiments, the precipitating step can be carried out in stages. In a first stage, the ethylene glycol can be cooled to a first temperature (e.g., 50° C.) to cause a first portion of the BHET to precipitate. Then, in a second stage, the ethylene glycol can be cooled to a second temperature less than the first temperature (e.g., below 10° C.) to cause a second portion of the BHET to precipitate. When precipitation is carried out in multiple stages, the separating step may be carried out just once following the last precipitation stage, or may be carried out in multiple stages, after each precipitation stage. The resultant BHET monomers (and PET oligomers, in certain embodiments) can then be purified and re-polymerized to form new, virgin PET.

According to a further embodiment exemplifying the principles of the invention, the depleted reaction product can be recycled by first distilling at least a portion of the depleted reaction product to produce a recycled ethylene glycol product. The depleted reaction product and/or the recycled ethylene glycol product can be used as components of a new reaction mixture, with the new reaction mixture. For example, the new reaction mixture can comprise the depleted reaction product, the recycled ethylene glycol product, and the catalytic system described herein (e.g., a catalyst and a microwave absorber). Optionally, or as needed, the reaction mixture can be supplemented with fresh PET, fresh ethylene glycol, and fresh catalytic system components as needed. The new reaction mixture can then be heated by microwave irradiation in order to degrade the PET within the depleted reaction product to its reactive intermediate(s), forming a BHET reaction product.

The reaction product is preferably a homogeneous product, where the BHET is dissolved in the ethylene glycol. It will be appreciated that some excess PET may remain in the reaction product in solid form after completion of the depolymerization process, depending on the specific reaction conditions and amount of PET per liter of ethylene glycol added. Remnant PET may be included in a subsequent batch of the depolymerization process, or it may be discarded.

Glycolytic depolymerization of PET typically results in the creation of three byproducts: mono(2-hydroxyethyl) terephthalate (MHET), bis(2-hydroxyethyl) terephthalate (BHET) and BHET dimer:

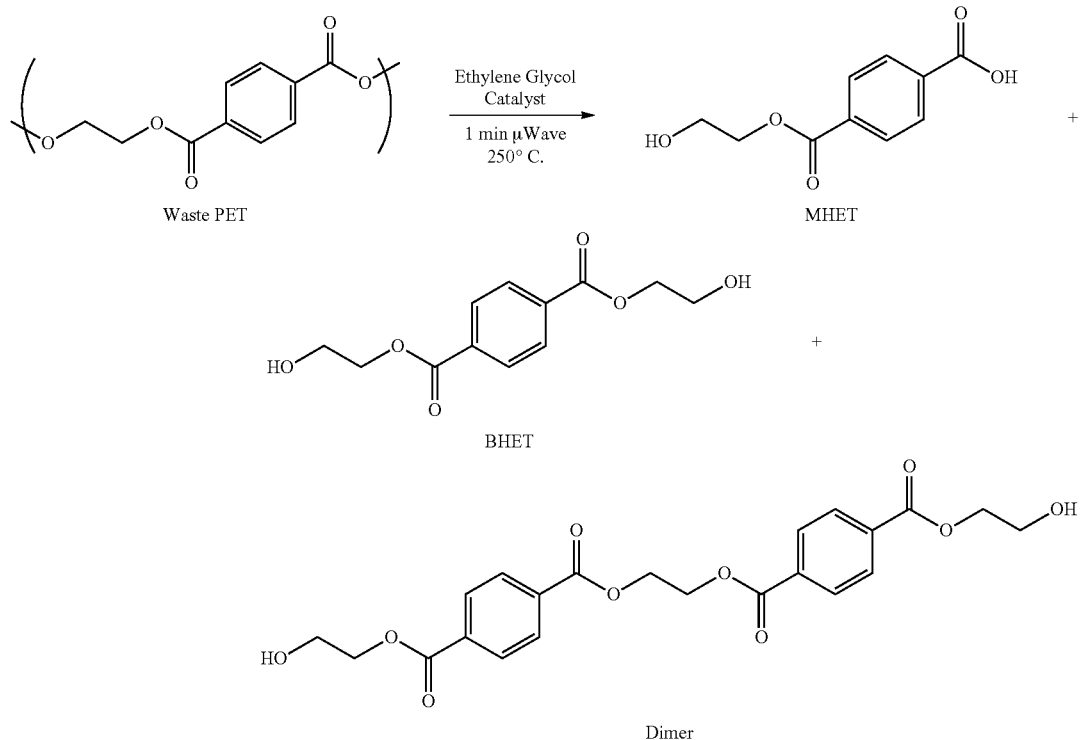

MHET is less reactive than BHET due to the presence of a pendant carboxylic acid group, which requires the formation of reactive intermediates before the melt polymerization reaction can be initiated to create new virgin PET. Therefore, to maximize the overall efficiency of recycling PET, it is desirable to reduce the yield of MHET and maximize the yield of BHET in the collective depolymerized byproduct.

In certain embodiments, a catalyst is selected which is capable of yielding greater than 80% by weight of BHET (in either monomeric or oligomeric form; e.g., dimeric, trimeric, tetrameric, pentameric, or higher oligomeric form) and less than 20% by weight of MHET. However, preferably, a catalyst is selected which is capable of yielding greater than 90% by weight of BHET and less than 10% by weight of MHET, and most preferably, greater than 95% by weight of BHET and less than 1% to 5% by weight of MHET. In some embodiments, between 60% and 98% by weight of the PET is converted to BHET in monomeric form in the reaction product, with not more than between 5% and 20% percent by weight of the PET being converted to BHET in an oligomeric form larger than trimeric, tetrameric, or pentameric form in the reaction product. In preferred embodiments, zinc salts are used as the catalyst. Most preferably, zinc acetate is used as the catalyst. In other embodiments, the catalyst can be selected from the group consisting of: sodium carbonate; sodium bicarbonate; sodium acetate; manganese acetate; magnesium acetate; zinc acetate; zinc chloride; 1,5,7-triazabicyclo[4.4.0]dec-5-ene (TBD); 1,8-diazabicyclo[5.4.0]undec-7-ene (DBU); 4-dimethylaminopyridine (DMAP), and combinations thereof.

Even with the use of microwave irradiation, PET recycling via glycolysis historically has been cost prohibitive due to the energy requirements of effectuating the depolymerization reaction. Thus, when attempting to maximize the overall efficiency of recycling PET, the amount of energy a particular catalyst requires to effectuate glycolytic depolymerization of PET is also an important factor in catalyst selection. Paradoxally, catalysts most effective at maximizing the yield of BHET, such as zinc acetate, were determined to require the most energy.

To reduce energy consumption while maintaining the speed and efficiency of the depolymerization reaction, it was discovered that a mixed catalytic system comprising both a catalyst and a microwave absorber could be utilized to provide a process that is significantly more energy efficient than current chemical recycling techniques. Preferably, a microwave absorber is selected which is capable of efficiently absorbing microwave irradiation while being inert during the PET degradation reaction. In preferred embodiments, sodium salts are used as the microwave absorber. Most preferably, sodium chloride is used as the microwave absorber. In other embodiments, the microwave absorber can be selected from the group consisting of: sodium salts, lithium salts, potassium salts, calcium salts, magnesium salts, or a combination thereof (e.g., sodium chloride, sodium bromide, sodium iodide, sodium fluoride, lithium chloride, potassium chloride, magnesium chloride, calcium chloride or a combination thereof).

In a preferred embodiment of the present invention, the catalyst is included in the reaction mixture in an amount of from 0.01, 0.02, 0.1 or 0.2 grams per liter of ethylene glycol up to 5, 10, 50 or 100 grams per liter of ethylene glycol; the microwave absorber is included in the reaction mixture in an amount of from 0.02, 0.04, 0.2, or 0.4 grams per liter of ethylene glycol up to 40, 100, or 400 grams per liter of ethylene glycol; and the PET is included in the reaction mixture in an any suitable amount, such as 10, 50, or 100 grams per liter of ethylene glycol, up to 250, 300, or 350 grams per liter of ethylene glycol.

EXAMPLES

The following examples, including the experiments conducted and the results achieved, are provided for illustrative purposes only and are not to be construed as limiting the present invention.

All chemicals for the following examples were purchased from Sigma-Aldrich or Fisher Scientific and used without any purification, unless otherwise noted. Post-consumer polyethylene terephthalate (pcPET) was sourced from used water bottles. PET bottles were shredded into 3 mm×5 mm flake using an office paper shredder. The PET flake was washed with tap water and dried in an oven held at 120° C. for a minimum of 4 hours. All reactions were carried out on a Biotage Initiator Classic with a 400-watt magnetron. High Performance Liquid Chromatography (HPLC) was run on an Agilent 1200 series HPLC system. The mobile phase consisted of mixtures of $H_2O$ with 0.1% TFA (solvent A) and acetonitrile with 0.1% TFA (solvent B). The elution protocol consisted of a gradient starting at 95:5 (A to B) and finishing at 0:100 (A to B) over 20 minutes. The analyte was eluted at a flow rate of 1 mL/min and monitored at a wavelength of 250 nm. Electricity consumption was monitored using a P3-International "Kill-A-Watt" or ThinkTank Energy Products "watts up?" electricity usage monitor. NMR spectra were collected on Varian 400 MHz spectrometer. H-NMR spectra were recorded at 400 MHz and C NMR spectra were recorded at 100 MHz.

Example 1

Example 1 demonstrates the effect of catalyst selection and catalyst concentration on the reaction efficiency of glycolytic depolymerization of PET to BHET. From a reaction standpoint, glycolytic depolymerization of PET is most efficient when the yield of BHET is maximized and the yield of MHET is minimized. The following catalysts were screened for their efficiency at depolymerizing PET into BHET: imidazole, triethyl amine (TEA), pyridine, antimony oxide, copper acetate, sodium carbonate, sodium bicarbonate, sodium acetate, manganese acetate, 1,5,7-triazabicyclo [4.4.0]dec-5-ene (TBD), 1,8-diazabicyclo[5.4.0]undec-7-ene (DBU), magnesium acetate, 4-dimethylaminopyridine (DMAP), zinc chloride and zinc acetate. As shown below, it was discovered that the yield of BHET from glycolytic depolymerization of PET is dependent on the particular catalyst being utilized, the concentration of the catalyst, and the duration of microwave irradiation.

For this investigation, pcPET flakes (0.500 g, 2.60 mmol of repeat unit) and a catalyst (50 mg) were suspended in ethylene glycol (5 mL) to form a heterogeneous mixture within a 5 mL microwave vial equipped with a magnetic stir bar. Each reaction mixture was inserted into the microwave reactor and heated to 250° C. and held at 250° C. for 1 minute. The microwave reactor was set to high absorption unless otherwise noted. Upon completion, a successful degradation reaction was determined by: 1) a clear and colorless solution and/or 2) quantitative HPLC analysis of the reaction products. All reactions were completed in triplicate to determine accurate yields of BHET, MHET and BHET Dimer. PET and ethylene glycol were utilized in a 1:10 weight-to-volume ratio (PET:EG), with a reaction run-time of 1 minute and a reaction temperature of 250° C.

Catalysts that successfully degraded PET in 1-minute under microwave irradiation are reported in Table 1:

TABLE 1

| Catalyst | % Catalyst (w/w of PET) | % Yield of BHET | % Yield of MHET | % Yield of Dimer |
|---|---|---|---|---|
| Sodium Carbonate | 10% | 66.68 ± 2.38% | 28.84 ± 2.25% | 2.28 ± 0.02% |
| Sodium Bicarbonate | 10% | 76.73 ± 3.52% | 19.47 ± 3.37% | 2.61 ± 0.10% |
| Sodium Acetate | 10% | 80.63 ± 1.86% | 15.70 ± 1.79% | 2.56 ± 0.05% |
| Manganese Acetate | 10% | 84.89 ± 1.18% | 10.93 ± 1.21% | 2.85 ± 0.03% |
| TBD-super base | 10% | 85.05 ± 0.82% | 11.86 ± 0.82% | 2.38 ± 0.05% |
| DBU-super base | 10% | 86.93 ± 1.05% | 10.32 ± 0.62% | 1.94 ± 0.12% |
| Magnesium Acetate | 10% | 91.11 ± 0.41% | 5.10 ± 0.33% | 2.91 ± 0.03% |
| DMAP-organic base | 10% | 94.10 ± 0.97% | 1.75 ± 0.17% | 4.61 ± 0.85% |
| Zinc Chloride | 10% | 95.13 ± 0.09% | 0.60 ± 0.04% | 3.52 ± 0.09% |
| Zinc Acetate | 10% | 95.59 ± 0.06% | 0.97 ± 0.09% | 3.45 ± 0.09% |

Zinc salts were shown to be the most effective catalysts for glycolytic depolymerization of PET to BHET via microwave irradiation, with both zinc chloride and zinc acetate providing the BHET byproduct in excess of 95%. Furthermore, the total amount of reactive starting material suitable for melt (re)polymerization—i.e., the combined concentration of BHET and the BHET dimer—was shown to be greater than 99%.

Next, the catalyst concentration was investigated to determine the minimum amount of the catalyst needed to instigate the depolymerization reaction. The following standard reaction conditions were used: 0.5 g post-consumer PET, 5 mL ethylene glycol, 1 minute microwave reaction (high absorption) at 250° C., and variable amounts of zinc acetate. Specifically, zinc acetate dihydrate was used at the following concentrations: 50 mg, 10 mg, 5 mg, 4 mg, 3 mg, 2 mg, 1 mg, and 0.5 mg. PET and ethylene glycol were utilized in a 1:10 weight-to-volume ratio (PET:EG). Each catalytic concentration was run in triplicate and each reaction was analyzed by HPLC. The results are reported in Table 2:

TABLE 2

| Rxn Time (min) | Catalyst | % Catalyst (w/w of PET) | % Yield of BHET | % Yield of MHET | % Yield of Dimer |
|---|---|---|---|---|---|
| 1 | Zinc Acetate | 10% | 95.59 ± 0.06% | 0.97 ± 0.09% | 3.45 ± 0.09% |
| 1 | Zinc Acetate | 2% | 95.04 ± 0.06% | 0.93 ± 0.01% | 3.45 ± 0.06% |
| 1 | Zinc Acetate | 1% | 95.10 ± 0.23% | 0.65 ± 0.03% | 3.61 ± 0.08% |
| 1 | Zinc Acetate | 0.8% | 95.44 ± 0.20% | 0.55 ± 0.05% | 3.51 ± 0.11% |
| 1 | Zinc Acetate | 0.6% | 95.49 ± 0.29% | 0.54 ± 0.05% | 3.49 ± 0.17% |
| 1 | Zinc Acetate | 0.4% | 95.32 ± 0.07% | 0.48 ± 0.01% | 3.51 ± 0.03% |
| 1 | Zinc Acetate | 0.2% | 86.73 ± 0.49% | 0.65 ± 0.04% | 9.56 ± 0.34% |
| 1 | Zinc Acetate | 0.1% | 49.16 ± 2.57% | 1.09 ± 0.04% | 28.21 ± 0.55% |
| 2 | Zinc Acetate | 0.2% | 94.96 ± 0.91% | 0.44 ± 0.02% | 3.64 ± 0.06% |
| 5 | Zinc Acetate | 0.1% | 94.29 ± 0.39% | 0.57 ± 0.04% | 4.03 ± 0.14% |

As shown in Table 2, zinc acetate could be reduced from 10 weight percent (wt %, w/w of PET) down to 0.4 wt % (2 mg) without any significant decrease to the yield of BHET. This was a 25-fold reduction in the amount of catalyst being utilized without an effect on the yield of BHET. Moreover, zinc acetate was shown to be able to be reduced to 0.2 wt % (50-fold) and even 0.1 wt % (100-fold) provided that the reaction time was increased to 2 minutes and 5 minutes, respectively.

Example 2

Example 2 demonstrates the effect of ethylene glycol concentration on the reaction efficiency of glycolytic depolymerization of PET to BHET. Generic reaction conditions were used to identify the minimal amount of solvent required for the fast and efficient depolymerization of pcPET. The following standard reaction conditions were used: 0.4 wt % catalyst (i.e. 2 mg of catalyst for 0.5 g of PET or 4 mg of catalyst for 1 g PET), 5 mL ethylene glycol, 1 minute microwave reaction (high absorption) at 250° C., and variable amounts of post-consumer PET. Specifically, the following ratios of ethylene glycol (volume) to PET (weight) were investigated: 20:1 (5 mL EG:250 mg PET), 10:1 (5 mL EG:500 mg PET), 8:1 (5 mL EG:625 mg PET), 6:1 (5 mL EG:833 mg PET), 5:1 (5 mL EG:1 g PET), 4:1 (5 mL EG:1.25 g PET). Each ratio was run in triplicate and each reaction was analyzed by HPLC. The effect of ethylene glycol concentration on the yield of BHET, MHET, and BHET dimer are reported in Table 3:

TABLE 3

| Ethylene Glycol:PET (w/w) | % Yield of BHET | % Yield of MHET | % Yield of Dimer |
|---|---|---|---|
| 20:1 | 95.26 ± 0.60% | 0.70 ± 0.07% | 3.28 ± 1.06% |
| 10:1 | 95.32 ± 0.07% | 0.48 ± 0.01% | 3.51 ± 0.03% |
| 8:1 | 94.25 ± 0.05% | 0.42 ± 0.01% | 4.59 ± 0.02% |
| 6:1 | 92.68 ± 0.12% | 0.47 ± 0.03% | 6.01 ± 0.05% |
| 5:1 | 91.89 ± 0.06% | 0.44 ± 0.01% | 6.75 ± 0.03% |
| 4:1 | 89.87 ± 0.15% | 0.45 ± 0.02% | 8.51 ± 0.13% |

These results demonstrate that the solvent-to-PET ratio could be reduced to 4:1 (w:w) without any significant increase in the production of MHET.

Example 3

Example 3 demonstrates the effect of catalyst selection on both reaction efficiency and overall energy consumption during glycolytic depolymerization of PET. The wattage, time, and watt-hours of the glycolytic depolymerization reaction using the following catalysts were investigated: imidazole, triethyl amine (TEA), pyridine, antimony oxide, copper acetate, sodium carbonate, sodium bicarbonate, sodium acetate, manganese acetate, 1,5,7-triazabicyclo[4.4.0]dec-5-ene (TBD), 1,8-diazabicyclo[5.4.0]undec-7-ene (DBU), magnesium acetate, 4-dimethylaminopyridine (DMAP), zinc chloride and zinc acetate. Electricity usage was monitored using a P3-International "Kill-A-Watt" electricity monitor. Reaction conditions included a 1:10 PET-to-EG ratio (0.5 g of pcPET, 5 mL of ethylene glycol), 10% w/w of each catalyst (50 mg of each catalyst), with the reaction time being set to one (1) minute microwave reaction (high absorption) at 250° C. The results of the comparative study are reported in Table 4 below:

TABLE 4

| Catalyst | % Yield of BHET | % Yield of MHET | % Yield of Dimer | Power (watt*hour) |
|---|---|---|---|---|
| Sodium Carbonate | 66.68 ± 2.38% | 28.84 ± 2.25% | 2.28 ± 0.02% | 10.09 ± 0.63% |
| Sodium Bicarbonate | 76.73 ± 3.32% | 19.47 ± 3.37% | 2.61 ± 0.10% | 12.85 ± 0.18% |
| Sodium Acetate | 80.83 ± 1.86% | 15.70 ± 1.79% | 2.56 ± 0.05% | 14.38 ± 1.46% |
| TBD-super base | 85.05 ± 0.82% | 11.86 ± 0.82% | 2.38 ± 0.05% | 15.66 ± 1.04% |
| DBU-super base | 86.93 ± 1.05% | 10.32 ± 0.62% | 1.94 ± 0.12% | 21.36 ± 0.03% |
| Zinc Chloride | 95.13 ± 0.09% | 0.60 ± 0.04% | 3.52 ± 0.09% | 34.90 ± 1.16% |
| Magnesium Acetate | 91.11 ± 0.41% | 5.10 ± 0.33% | 2.91 ± 0.03% | 40.40 ± 1.25% |
| Manganese Acetate | 84.89 ± 1.18% | 10.93 ± 1.21% | 2.85 ± 0.03% | 43.33 ± 1.43% |
| DMAP-organic base | 94.10 ± 0.09% | 1.75 ± 0.17% | 4.61 ± 0.85% | 44.40 ± 3.91% |
| Zinc Acetate | 95.59 ± 0.06% | 0.97 ± 0.09% | 3.45 ± 0.09% | 56.40 ± 2.03% |

As shown in Table 4, zinc acetate provided the greatest reaction efficiency (i.e., the most efficient at accelerating the glycolytic depolymerization of PET to BHET), but was the least energy efficient. Conversely, the most energy efficient catalysts were salts of sodium, but they exhibited marginal reaction efficiency.

Example 4

Example 4 demonstrates the beneficial effect of using a catalytic system comprising a microwave absorber on the overall energy consumption of glycolytic depolymerization of PET. In Example 3, sodium salts were shown to be the most energy efficient catalysts. However, sodium carbonate, sodium bicarbonate and sodium acetate each function to degrade PET and generate a high percentage of MHET during the glycolytic depolymerization process. Thus, sodium chloride—an inert sodium salt—was hypothesized as being an ideal microwave absorber because it is inert during the degradation reaction yet could efficiently absorb microwave irradiation.

For this investigation, pcPET flakes (0.500 g, 2.60 mmol of repeat unit), zinc acetate dihydrate catalyst (5 mg, 0.023 mmol), and a microwave absorber (25 mg) were suspended in ethylene glycol (5 mL) to form a heterogeneous mixture within a 5 mL microwave vial equipped with a magnetic stir bar. The reaction mixture was inserted into the microwave reactor and heated to 250° C. and held at 250° C. for 2 minutes. The microwave reactor was set to high absorption. Upon completion, a successful degradation reaction was determined by: 1) a clear and colorless solution and/or 2) quantitative HPLC analysis of the reaction product. All reactions were completed in triplicate to determine accurate yields of BHET, MHET and BHET dimer. For all reactions, power consumption was monitored using a P3-International "Kill-A-Watt" electricity monitor. The results are reported in Table 5:

TABLE 5

| Absorber | % Absorber (w/w of PET) | Power (watt*hr) | % Yield of BHET | % Yield of MHET | % Yield of Dimer |
|---|---|---|---|---|---|
| Sodium Chloride | 0% | 52.96 ± 3.82% | 95.32 ± 0.18% | 0.65 ± 0.03% | 3.62 ± 0.09% |
| Sodium Chloride | 5% | 14.01 ± 0.21% | 93.31 ± 0.10% | 2.32 ± 0.02% | 3.83 ± 0.04% |

This investigation demonstrated that adding 25 mg (5 wt %) of sodium chloride reduced energy consumption from 53 watt*hr down to 14 watt*hr. This was a 75% decrease (3.8-fold) in energy consumption, with a corresponding decrease of BHET yield of only 2%.

Example 5

Example 5 demonstrates the effect of microwave absorber concentration on both the reaction efficiency and energy efficiency of glycolytic depolymerization of PET to BHET. For this investigation, pcPET flakes (0.500 g, 2.60 mmol of repeat unit), a zinc acetate dihydrate catalyst (5 mg, 0.023 mmol), and variable amounts of sodium chloride (5, 10, 15, 20 and 25 mg) were suspended in ethylene glycol (5 mL) to form a heterogeneous mixture within a 5 mL microwave vial equipped with a magnetic stir bar. The reaction mixture was inserted into the microwave reactor and heated to 250° C. and held at 250° C. for 2 minutes. The microwave reactor was set to high absorption. Upon completion, a successful degradation reaction was determined by: 1) a clear and colorless solution and/or 2) quantitative HPLC analysis of the reaction product. All reactions were completed in triplicate to determine accurate yields of BHET, MHET and BHET dimer. For all reactions, power consumption was monitored using a P3-International "Kill-A-Watt" electricity monitor. The results are reported in Table 6:

TABLE 6

| Absorber | % Absorber (w/w of PET) | Power (watt*hr) | % Yield of BHET | % Yield of MHET | % Yield of Dimer |
|---|---|---|---|---|---|
| Sodium Chloride | 0% | 52.96 ± 3.82% | 95.32 ± 0.18% | 0.65 ± 0.03% | 3.62 ± 0.09% |
| Sodium Chloride | 1% | 27.57 ± 0.68% | 94.49 ± 0.34% | 1.55 ± 0.20% | 3.71 ± 0.15% |
| Sodium Chloride | 2% | 22.73 ± 0.60% | 94.03 ± 0.22% | 1.99 ± 0.12% | 3.68 ± 0.05% |
| Sodium Chloride | 3% | 18.27 ± 0.16% | 93.98 ± 0.35% | 1.97 ± 0.18% | 3.73 ± 0.09% |
| Sodium Chloride | 4% | 14.37 ± 0.14% | 93.14 ± 0.25% | 2.24 ± 0.11% | 4.06 ± 0.18% |
| Sodium Chloride | 5% | 14.01 ± 0.21% | 93.31 ± 0.10% | 2.32 ± 0.02% | 3.83 ± 0.04% |

This investigation demonstrated that only a small amount of sodium chloride was needed to reduce energy consumption. The addition of 5 mg (1 wt %) of sodium chloride reduced energy consumption by 52% (1.9-fold), with energy consumption continuing to decrease until a plateau was reached (a 3.8-fold decrease in energy consumption) with approximately 20-25 mg (4-5 wt %) of sodium chloride. The HPLC assay revealed that the addition of sodium chloride reduced the BHET yield and increased the MHET yield, but only a small decrease of 2% (from 95.32±0.183% to 93.31±0.103%) was observed for BHET, and a small increase of 1.6% (from 0.65±0.031% to 2.24±0.107%) was observed for MHET. Furthermore, the amount of viable starting material (BHET+Dimer) present in the reaction mixture was >97% and only decreased 1.75% (from 98.95±0.269% to 97.20±0.430%).

Example 6

Example 6 demonstrates the energy consumption associated with the glycolytic depolymerization of pcPET using a mixed catalytic system comprising one of several different microwave absorbers. The following microwave absorbers were tested: sodium chloride, sodium bromide, sodium iodide, sodium fluoride, lithium chloride, potassium chloride, magnesium chloride, calcium chloride, and copper chloride. For this investigation, pcPET flakes (0.500 g, 2.60 mmol of repeat unit), zinc acetate dihydrate catalyst (5 mg, 0.023 mmol), and a microwave absorber (20 mg) were suspended in ethylene glycol (5 mL) to form a heterogeneous mixture within a 5 mL microwave vial equipped with a magnetic stir bar. Each reaction mixture was inserted into the microwave reactor and heated to 250° C. and held at 250° C. for 2 minutes. The microwave reactor was set to high absorption. Upon completion, a successful degradation reaction was determined by: 1) a clear and colorless solution and/or 2) quantitative HPLC analysis of the reaction products. All reactions were completed in triplicate to determine accurate yields of BHET, MHET and BHET dimer. For all reactions, power consumption was monitored using a Think-Tank Energy Products "Watts up?" watt meter/power analyzer.

First, a catalytic system comprising a variety of sodium salts (sodium chloride, sodium bromide, sodium iodide, and sodium fluoride) were compared against a catalytic system comprising only a catalyst to determine whether any improved efficiency could be achieved through the use of a mixed catalytic system. The results of this comparative study are reported in Table 7 below:

TABLE 7

| Absorber | % Absorber (w/w of PET) | Power (watt*hour) |
|---|---|---|
| Sodium Chloride | 4% | 17.50 ± 0.10% |
| Sodium Bromide | 4% | 20.73 ± 0.84% |
| Sodium Iodide | 4% | 23.43 ± 0.51% |

TABLE 7-continued

| Absorber | % Absorber (w/w of PET) | Power (watt*hour) |
|---|---|---|
| Sodium Fluoride | 4% | 26.50 ± 0.60% |
| No Absorber | 0% | 77.40 ± 8.12% |

This experiment showed that sodium chloride was the most efficient absorber requiring only 17.5 watt*hour of power. This was followed by sodium bromide (20.7 watt*hr), sodium iodide (23.4 watt*hr) and sodium fluoride (26.5 watt*hr). In comparison, pcPET degradation without the use of a microwave absorber required 77.4 watt*hr, or 4.4 times the power to bring the reaction to completion.

Next, a catalytic system comprising a variety of chloride salts (lithium chloride, sodium chloride, potassium chloride, magnesium chloride, calcium chloride, and copper chloride) were compared against a catalytic system comprising only a catalyst to determine whether any improved efficiency could be achieved through the use of a mixed catalytic system. The results of this comparative study are reported in Table 8 below:

TABLE 8

| Absorber | % Absorber (w/w of PET) | Power (watt*hour) |
|---|---|---|
| Lithium Chloride | 4% | 16.80 ± 0.56% |
| Sodium Chloride | 4% | 17.50 ± 0.10% |
| Potassium Chloride | 4% | 17.73 ± 0.40% |
| Magnesium Chloride | 4% | 22.80 ± 0.52% |
| Calcium Chloride | 4% | 23.40 ± 1.13% |
| No Absorber | 0% | 77.40 ± 8.12% |

Lithium chloride was discovered to be the most efficient microwave absorber, requiring only 16.8 watt*hour of power. It was followed by sodium chloride (17.5 watt*hr), potassium chloride (17.7 watt*hr), magnesium chloride (22.8 watt*hr), and calcium chloride (23.4 watt*hr). Incomplete depolymerization was observed for the reactions utilizing copper chloride.

Example 7

Example 7 demonstrates the effect of utilizing one of several different microwave absorbers on BHET yield and MHET yield during the glycolytic depolymerization of pcPET. A high performance liquid chromatography (HPLC) assay was used for this investigation. It was discovered that the addition of the microwave absorbers only marginally reduced the BHET yield and only slightly increased the MHET yield. The results are reported in Table 9 below:

TABLE 9

| Absorber | % Absorber (w/w of PET) | % Yield of BHET | % Yield of MHET | % Yield of Dimer |
|---|---|---|---|---|
| Sodium Iodide | 4% | 97.50 ± 0.32% | 1.42 ± 0.04% | 1.09 ± 0.32% |
| Sodium Bromide | 4% | 96.30 ± 0.74% | 1.65 ± 0.10% | 2.05 ± 0.84% |
| Calcium Chloride | 4% | 96.15 ± 0.14% | 2.26 ± 0.04% | 1.23 ± 0.10% |
| Lithium Chloride | 4% | 95.44 ± 0.72% | 2.83 ± 0.07% | 1.73 ± 0.78% |
| Potassium Chloride | 4% | 95.00 ± 0.22% | 2.24 ± 0.04% | 2.77 ± 0.24% |
| Sodium Chloride | 4% | 94.74 ± 0.30% | 2.46 ± 0.09% | 2.80 ± 0.21% |
| Magnesium Chloride | 4% | 94.32 ± 0.55% | 3.20 ± 0.02% | 2.48 ± 0.54% |
| Sodium Fluoride | 4% | 94.03 ± 0.21% | 3.32 ± 0.09% | 2.65 ± 0.17% |
| No Absorber | 0% | 96.48 ± 0.78% | 0.53 ± 0.05% | 2.99 ± 0.82% |

Across all potential absorbers, there was little change in BHET yield from the no-absorber reaction (96.5%) to sodium fluoride (94.0%). The percent yield for BHET ranged between these 94-98% for all the remaining absorbers with sodium iodide giving the highest BHET yield at 97.5%. Conversely, the percent yield of the MHET increased from the no-absorber reaction (0.5%) to sodium fluoride (3.3%). The percent yield for MHET ranged between 1.4-3.3% for all the remaining absorbers with sodium iodide giving the lowest MHET yield at 1.4%.

The foregoing experiments demonstrate that, when used in a mixed catalytic system, sodium salts, lithium salts, potassium salts, calcium salts, and magnesium salts are effective at reducing the energy consumption of glycolytic depolymerization of pcPET via microwave irradiation while having a minimal effect on the degradation reaction itself. A lithium chloride absorber was discovered to reduce the energy consumption the most, while a sodium iodide absorber had the least effect on the reaction.

The foregoing description and examples demonstrate the principles, exemplary embodiments, and modes of operation of the invention. However, the invention should not be construed as being limited to the particular embodiments discussed above. Many modifications of the embodiments described herein will come to mind to one skilled in the art having the benefit of the teaching presented in the foregoing descriptions and the associated drawings. Accordingly, it should be appreciated that variations to those embodiments can be made by those skilled in the art without departing from the scope of the invention.

What is claimed is:

1. A method of making bis(2-hydroxyethyl) terephthalate (BHET) from polyethylene terephthalate (PET), comprising:
   (a) combining PET with ethylene glycol and a catalyst system to produce a heterogeneous reaction mixture, wherein the catalytic system comprises a catalyst and a microwave absorber, wherein the microwave absorber is selected from the group consisting of: sodium chloride, sodium bromide, sodium iodide, sodium fluoride, lithium chloride, potassium chloride, magnesium chloride, and calcium chloride; and then
   (b) heating by microwave irradiation the reaction mixture to produce a reaction product comprising BHET.

2. The method of claim 1, wherein the microwave absorber comprises a sodium salt, lithium salt, potassium salt, calcium salt, a magnesium salt, or combination thereof.

3. The method of claim 1, wherein the catalyst is selected from the group consisting of: zinc acetate, zinc chloride, manganese acetate, 1,5,7-triazabicyclo[4.4.0]dec-5-ene (TBD), 1,8-diazabicyclo[5.4.O]undec-7-ene (DBU), magnesium acetate, 4-dimethylaminopyridine (DMAP), and combinations thereof.

4. The method of claim 1, wherein the microwave absorber comprises sodium chloride.

5. The method of claim 1, wherein the catalyst comprises zinc acetate.

6. The method of claim 3, wherein the heating step (b) comprises heating by microwave irradiating the reaction mixture to a temperature greater than the boiling point of ethylene glycol.

7. The method of claim 3, wherein the heating step (b) comprises heating by microwave irradiating the reaction mixture to a temperature of at least the melting point of the PET.

8. The method of claim 3, wherein at least 90 percent by weight of the PET is converted to BHET.

9. The method of claim 3, wherein not more than 10 percent by weight of the PET is converted to mono(2-hydroxyethyl) terephthalate (MHET) in the reaction product.

10. The method of claim 3, further comprising the steps of:
    (c) precipitating the BHET in the reaction product; and then
    (d) separating the BHET from the reaction product to produce solid BHET and a depleted reaction product.

11. The method of claim 10, wherein the precipitating step is carried out by cooling the reaction product to at least a first temperature less than 60° C.

12. The method of claim 10, wherein the precipitating step (c) is carried out in stages, the stages comprising:
    (i) a first stage at a first temperature to which the reaction product is cooled and during which a first portion of the BHET precipitates, followed by
    (ii) a second stage at a second temperature less than the first temperature during which a second portion of the BHET precipitates.

13. The method of claim 12, wherein the precipitating step (c) further comprises mixing said reaction product with water.

14. The method of claim 13, wherein the separating step (d) is carried out by sedimentation, centrifugation, filtration, or a combination thereof.

15. The method of claim 10, further comprising the steps of:
    (e) distilling at least a portion of the depleted reaction product to produce a recycled ethylene glycol product and solid BHET, and then:
    (f) repeating steps (c) through (d) at least once with the depleted reaction product, the recycled ethylene glycol product, or a combination thereof.

16. The method of claim 1, wherein: the catalyst is included in the reaction mixture in an amount of from 0.01, 0.02, 0.1 or 0.2 grams per liter of ethylene glycol, up to 5, 10, 50 or 100 grams per liter of ethylene glycol; the microwave absorber is included in the reaction mixture in an amount of from 0.02, 0.04, 0.2, or 0.4 grams per liter of ethylene glycol, up to 40, 100, or 400 grams per liter of ethylene glycol; and the PET is included in the reaction mixture in an amount of from 10 or 50 grams per liter of ethylene glycol, up to 250 or 300 grams per liter of ethylene glycol.

* * * * *